(12) United States Patent
Wickham (10) Patent No.: US 9,662,455 B2
(45) Date of Patent: May 30, 2017

(54) SEGMENTED SAFETY COVER FOR NEEDLE DELIVERY

(71) Applicant: NPA LIMITED, Auckland (NZ)

(72) Inventor: Henry Wickham, Auckland (NZ)

(73) Assignee: NPA LIMITED, Auckland (NZ)

( * ) Notice: Subject to any disclaimer, the term of this patent is extended or adjusted under 35 U.S.C. 154(b) by 0 days.

(21) Appl. No.: 15/089,390

(22) Filed: Apr. 1, 2016

(65) Prior Publication Data

US 2017/0065772 A1   Mar. 9, 2017

(51) Int. Cl.
*A61M 5/32* (2006.01)
*A61B 10/02* (2006.01)
*A61B 5/15* (2006.01)

(52) U.S. Cl.
CPC ..... *A61M 5/3204* (2013.01); *A61B 5/150656* (2013.01); *A61B 10/02* (2013.01); *A61M 5/3216* (2013.01)

(58) Field of Classification Search
CPC ........ A61M 5/3216; A61M 2005/3267; A61M 5/3219; Y10S 128/919; A61B 5/150633
See application file for complete search history.

(56) References Cited

U.S. PATENT DOCUMENTS

| | | |
|---|---|---|
| 4,735,618 A | 4/1988 | Hagen et al. |
| 4,935,013 A | 6/1990 | Haber et al. |
| 4,955,866 A | 9/1990 | Corey et al. |
| 4,994,034 A | 2/1991 | Botich et al. |
| 5,188,599 A | 2/1993 | Botich et al. |
| 5,250,031 A | 10/1993 | Kaplan et al. |
| 5,256,152 A | 10/1993 | Marks |
| 5,295,972 A | 3/1994 | Mischenko et al. |
| 5,348,544 A | 9/1994 | Sweeney et al. |
| 5,584,818 A | 12/1996 | Morrison |
| 5,634,909 A | 6/1997 | Schmitz |
| 5,910,130 A | 6/1999 | Caizza et al. |
| 6,280,420 B1 * | 8/2001 | Ferguson ............ A61M 5/3275 604/192 |
| 7,090,656 B1 | 8/2006 | Botich et al. |
| 7,361,159 B2 | 4/2008 | Fiser et al. |
| 7,534,232 B2 | 5/2009 | Iwase et al. |

(Continued)

FOREIGN PATENT DOCUMENTS

EP    654281 B1    7/2001

*Primary Examiner* — Emily Schmidt
(74) *Attorney, Agent, or Firm* — Mark A. Litman & Associates, P.A.

(57) ABSTRACT

A segmented safety cover may include:
 a) a proximal segment combined with a needle hub;
 b) a needle cannula that extends from the proximal needle hub to a distal sharpened end;
 c) a distal end cap with a hollow bore through which the cannula shaft passes;
 d) a centrally mounted toggle locking mechanism, separating the proximal needle hub from the distal end cap;
 e) the toggle locking mechanism is torsion spring assisted;
 f) a proximal cover segment is connected to the hub via a proximal hinge and a distal cover segment is connected to the end cap via a distal hinge;
 g) said proximal cover segment and said distal cover segment of said toggle locking mechanism being configured with abutting faces when the segmented safety cover is in a safety mode; and
 h) wherein the proximal hinge, abutting faces and distal hinge are in line in the safe mode.

22 Claims, 8 Drawing Sheets

(56) References Cited

U.S. PATENT DOCUMENTS

| | | |
|---|---|---|
| 9,005,232 B2 | 4/2015 | Kim et al. |
| 2002/0165498 A1* | 11/2002 | Ward, Jr. ............. A61B 5/1438 604/198 |
| 2005/0209567 A1* | 9/2005 | Sibbitt, Jr. ........... A61B 5/1405 604/187 |
| 2007/0078409 A1 | 4/2007 | Saltz et al. |
| 2008/0132838 A1 | 6/2008 | Wyrick et al. |
| 2010/0100039 A1 | 4/2010 | Wyrick et al. |
| 2011/0066107 A1 | 3/2011 | Stephens et al. |
| 2011/0226646 A1 | 9/2011 | Wyrick et al. |

* cited by examiner

SEGMENTED SAFETY COVER FOR NEEDLE DELIVERY

RELATED APPLICATION DATA

This application claims priority under 35 U.S.C. 119 from New Zealand Patent Application Document No. 717018, filed 8 Sep. 2015.

BACKGROUND OF THE INVENTION

1. Field of the Invention

This invention relates to safety guards to protect against needle stick injuries used in medical and veterinary medical use of material delivery and material removal needles.

2. Background of the Art

According to the Occupational Safety and Health Administration (OSHA), needle stick injuries occur during all aspects of handling. 50% of incidents occur during the invasive procedure (while introducing needle, by accidental needle withdrawal during procedure, or during needle withdrawal at the end of the procedure).

Ironically, the vast majority of safety needle devices currently on the market only give protection to the healthcare worker after completion of the invasive procedure.

Examples of disclosures of safety devices which protect needles by moving a protective shield over the sharp end of the needle are bountiful. Most of the disclosures describe a technique where the needle tip is exposed by first removing a protective cap and where the protective shield is moved form a collapsed position proximal to the user to a distal and extended position to cover the needle tip only after the invasive procedure has been completed.

U.S. Pat. No. 9,005,232 (KIM) discloses a lancing system comprising a lancet with a handle portion and a needle bearing portion, the needle bearing portion retaining a thin needle protected by a safety cap. The safety cap includes first and second chambers, where the first chamber acts as a sheath and the second chamber having a surface positioned to compromise the structure of the needle when the needle bearing portion of the lancet body is inserted into the second chamber.

U.S. Pat. No. 7,361,159 (Fiser) describes a safety apparatus is provided which includes a needle hub having an arm extending therefrom and an extensible frame connected to the needle hub. The extensible frame includes a proximal segment that is hingedly connected to a distal segment. The extensible frame is resiliently biased from a retracted position to an extended position, wherein the arm releasably engages the proximal segment to fix the extensible frame in a position between the retracted position and the extended position. In an alternate embodiment, the safety apparatus includes an extensible frame including a proximal segment which is hingedly connected to a distal segment. A resilient member is coupled to the proximal segment and the distal segment. The resilient member is configured to bias the extensible frame from a retracted position to an extended position. A method for infusing fluids to a subject is disclosed.

U.S. Pat. No. 7,534,232 (Iwase) discloses an indwelling needle composed of a body having a closed end, a needle forming at the tip a sharp edge, a tubular hub retaining the proximal end of the needle and slideable along the main body, a protective cover slidable along the main body and projecting from the main body, and a spring elastically fitted between the body and the protective cover. When a first projection is lifted by actuating a lever provided on the body and retractable along with the protective cover relative to the body, the first projection is housed in a through hole and presses a second projection of the protective cover engaged with a second engaging portion toward the inner circumference, rendering an operative state. The resultant length of indwelling needle in operative state can be modified, inhibiting injury to patient. U.S. Pat. No. 7,090,656 describes a hypodermic injection system with a retractable needle wherein the needle retracts within an interior cavity of a syringe plunger, such that the needle is confined within the plunger. A spring biases the needle rearwardly into the plunger, and a needle retainer releasably retains the needle against the bias of the spring. The plunger has a frangible end, which dissociates when the plunger engages the needle retainer, allowing the coiled spring to eject the needle into the interior cavity of the plunger. A body fluid sampling embodiment employs the same functional elements except the plunger is shorter and contains a linking that communicates with a vacuum container. The container allows fluid sampling and provides the structure to release the spring retracting the needle. The retractable needle embodiment is also employed with an insertion needle that guides a catheter tube below the skin of a patient and into the vein, and allows retraction of the insertion needle thereby avoiding accidental pricking of the health care worker by the insertion needle.

U.S. Pat. No. 5,634,909 (Schmitz) discloses a hypodermic injection system utilizes disposable medicament ampules having self-contained needles operated by a re-useable actuator to extend the needle from complete enclosure within the ampule out and into the flesh and inject the medicament as it moves, the needle automatically retracting into the disposable ampule after exhausting its contents, completely eliminating any need to handle the exposed needle before or after use.

U.S. Pat. Nos. 5,188,599 and 4,994,034 (Botich) disclose a hypodermic injection system (7) with a retractable needle (9) wherein the needle (9) retracts within an interior cavity (71) of a syringe plunger (59), such that the needle (9) is confinedly held within the plunger (59). A cylindrical spring housing (21) has resilient fingers (23) which captures a spring (15) biasly holding a needle holder (11) against the retaining force of resilient fingers (23). The plunger (59) has a frangible end (65), which dissociates when the outwardly tapered shoulders (68) spread the resilient fingers (23), allowing the coiled spring (15) to eject the needle (9) and its holder (11) into the interior cavity (71) of the syringe plunger (59). A body fluid sampling embodiment employs the same functional elements except the plunger (59") is shorter and contains a linking needle (137) that communicates with a vacuum container (147). The container allows fluid sampling and provides the structure to release the spring (15") retracting the needle (9").

U.S. Pat. No. 4,955,866 (Corey) provides a recapping device for use with medical devices including all hollow and solid medical needles of the type used for entry into the body and into closed intravenous and intraarterial systems for access, sampling, and injection of medications, and are withdrawn after use. The recapping device includes a hollow sleeve encircling a portion of the needle and having a distal end aperture adapted to permit the sleeve to slide between a first position on the medical device wherein the needle is exposed to enable use of the needle, and a second position characterized by the distal end of the needle being contained within the distal end capped hollow sleeve, and the device may optionally contain a housing for a free-floating fenestrated disk, which, upon movement of the device to its second position wherein the tip of the needle exits the distal end aperture, shifts position to provide an obstruction at that aperture. A securing means for the hollow sleeve, such as a tether, is provided for permitting substantially free slidable movement of the hollow sleeve between the first and second positions.

US Published Patent Application Nos. 20080132838 20100100039 20110226646 (Wyrick) disclose a reloadable medicine injector and methods are described in which a barrel with a receiving cavity is adapted to slidably receive a syringe subassembly for axial movement therein. Upon removal of a safety and release of a syringe driver, the syringe driver moves forward and injects the syringe needle. A plurality of penetration controls are shown for controlling injection needle penetration depth. The penetration controls have an abutment and various lengths to provide different needle penetration depth positions. In one form of penetration control a sleeve is used against which the syringe or related parts contact. In another form the front return spring is used as a penetration control. A cushioning ring may be used to reduce syringe breakage. A load distribution and guide ring may be used to distribute loading applied to the syringe and help guide the moving syringe.

US Published Patent Application No. 20070078409 (Salyz) escribes a protective needle guard assembly features a hub that is removably secured to a reusable syringes, a first and a second needle extending outwardly from the hub in opposite directions, and a moveable sheath that moves about an outer surface of the syringe. The needle guard includes an engagement device that engages the moveable sheath to secure the moveable sheath in an extended position wherein the moveable sheath extends beyond the distal end of the first needle. The moveable sheath features a retracted position wherein the first needle is substantially exposed. A cavity formed in the hub substantially covers and protects the second needle.

Other relevant disclosures are included in U.S. Pat. Nos. 5,348,544; 5,910,130; 5,256,152; 4,935,013; 4,735,618; 5,250,031; 5,295,972; and 5,584,818; and US20110066107; and EP0 654281. Most of the disclosures describe a way of blocking the needle path by means of a metallic clip or rotating member located in the distal needle cap and this only after the invasive procedure has been completed. These disclosures still are not believed to offers high levels of security and additional advances are still needed. These disclosures are incorporated herein by reference in their entirety by reference.

SUMMARY OF THE INVENTION

A segmented safety cover may include:
a) a proximal segment combined with a needle hub;
b) a needle cannula that extends from the proximal needle hub to a distal sharpened end.
c) a distal end cap with a hollow bore through which the cannula shaft passes
d) A centrally mounted toggle locking mechanism, separating the proximal needle hub from the distal end cap, hingedly connected to both and maintaining the needle guard in a position where it completely covers the needle tip
e) wherein the toggle locking mechanism is torsion spring assisted and consist of proximal and distal cover segments which overlays the cannula shaft and is linked together through a central hinge
f) wherein the proximal cover segment is connected to the hub via a proximal hinge and the distal cover segment is connected to the end cap via a distal hinge g) said proximal cover segment and said distal cover segment of said toggle locking mechanism being configured with abutting faces that contact each other above said central hinge when the segmented safety cover is in a safety mode; and
h) wherein the proximal hinge, abutting faces and distal hinge are in line in the safe mode so that a force exerted on the distal end cap is translated directly onto the abutting faces above the central hinge thereby maintaining the device in its locked state.

The proximal hinge, distal hinge and central hinge are configured to form a triangle configuration when the segmented safety cover is in a delivery mode for a needle with the distal cover segment and the distal end cap slide with respect to the needle within the cannula. The proximal cover segment appears to rotate relative to the hub, and the distal cover segment appears to rotate relative to the sliding distal end cap as it slides horizontally with respect to the needle.

DETAILED DESCRIPTION OF THE INVENTION

This invention addresses shortcomings by enabling a device that renders the medical needle (e.g., injection, biopsy, sampling, and sensor needles) safe at all times. This invention device has the needle tip exposed by manual intervention just prior to being inserted into the patient. It then passively returns to its locked position while the needle is withdrawn from the patient.

This device of the invention has a hinged arm that is in its extended position prior to being used and where a protective cap and protective shield is integrated and thus not removed to offer protection at all times. The needle tip is exposed just prior to the invasive procedure by manually unlocking the device. It then automatically locks again as the needle is removed from the patient.

A segmented safety cover may include:
a) a proximal segment combined with a needle hub. The hub is a structural element that may abut, secures or connects the proximal segment to another component such as a support or medical delivery or removal system (e.g., syringes, vacuum pressure, sampling pressure, sensing electronics, etc.);
b) a needle cannula that is mounted in the needle hub and extends from the hub to a distal sharpened end
c) a distal end cap with a hollow bore through which a cannula shaft passes. The segments and other components are made of substantive structural material that will not bend or distort under common forces encountered during normal use. The various segments of the cover may comprise polymeric materials (thermoplastic or thermoset), metallic materials, ceramics, composites or the like. Transparent, opaque or translucent materials may be used;
d) an engaged, torsion spring assisted, centrally hinged toggle locking mechanism that overlays the cannula shaft; The spring must be a resilient material, such as metals, or polymers that do not elastically deform during the full motion of the segments.
e) wherein the toggle locking mechanism consist of a proximal and distal cover segments linked together through a central hinge.
f) The central hinge is also preferably a full construction that allows rotation of one side (top or bottom) of the distal and proximal cover segments, such as the abutting sides.
g) said proximal cover segment and said distal cover segment are configured with abutting faces that contact each other above (not necessarily along the entire abutting faces, but at least the tops of those faces) said central hinge when the segmented safety cover is in a safety mode;
h) said proximal cover segment is hingedly connected to said proximal needle hub and said distal cover segment is hingedly connected to said distal end cap
i) wherein the proximal hinge, abutting faces and distal hinge are in line and the central hinge below the abutting faces so that any force exerted on the distal end cap would be translated directly onto the abutting faces thereby maintaining the device in its locked and safe state.

The proximal, distal and central hinge are configured to form a triangle configuration when the segmented safety cover is in a delivery mode for a needle with the distal cover segment rotated in a clockwise direction away from the proximal cover segment and the distal cover segment appears to rotate clockwise towards and with respect to the distal end cap as the distal end cap slides horizontally with respect to the needle.

The segmented safety cover will have a needle present in the needle hub and an injection end of the needle is within the distal end cap during a medical procedure. Upon forming the triangular configuration, the distal end cap is configured to retract over the needle and towards the needle hub, the distal segment appears to rotate with respect to the distal end cap as the distal end cap retracts and exposes the injection end of the needle. In the safety mode, the distal segment and proximal segment are in a locked mode, resisting movement of the distal segment and the proximal segment by the torsion spring.

Two manually operated pressure plates overlap sides of the distal cover segment and the proximal cover segment and the plates are configured to unlock the locked mode when pressure is applied to the two pressure plates.

The pressure plates are resiliently biased to dislocate from the unlocked mode to return to a locked ready mode when triggered by said distal end cap as it pushes against a patient's skin during the injection procedure. This frees the device to return to its initial locked mode as the needle is withdrawn from the patient.

A double (or second) locking mechanism is configured to establish the locked mode and the locking mechanism extends across a top of the abutting faces of the distal segment and the proximal segment.

The locking mechanism may have a clip on the proximal segment that snaps into a receiving opening on the distal segment. The clip may fit into an expandable slot and permanently locks the device in the safe mode to eliminate re-use, A reverse connection may be provided where the locking mechanism comprises a clip on the distal segment that snaps into a receiving opening on the proximal segment.

The torsion spring may be a single or preferably a double coil spring with a first extension of the double coil spring extending approximately parallel to the distal cover segment in the safety mode, and a second extension of the double coil spring extending approximately parallel to the proximal cover segment in the safety mode. The first one coil of the double coil spring may be on a first side of the cannula shaft and a second one coil of the double coil spring may be on a second and opposite side of the cannula shaft with respect to the first coil.

The segmented safety cover will have a needle present within the cover, and the segmented safety cover is configured so that the pointed injection end of the needle is completely covered by the distal end cap when the torsion spring is secured in the safety mode, and the pointed injection end of the needle is exposed out of the distal end cap when the safety mode is removed and compressive force applied by the torsion spring retracts the distal end cap by rotation of both the proximal cover segment and the distal arm about the central hinge.

A method for enabling injection of fluids using the segmented safety cover with a needle present within the cover of the present technology may include applying force to both the proximal arm and the distal arm from the torsion spring to elevate the central hinge and retract the distal end cap to slide the hollow bore within the distal end cap over the needle to expose the needle.

A segmented safety cover may be alternatively described as including:
  a) A proximal segment fixed with a needle hub, said proximal segment also being integrated with a syringe body or a blood collecting needle;
  b) A distal end cap with a hollow bore that covers a cannula shaft through which a needle may pass;
  c) A rigidly interlocked, torsion spring assisted centrally hinged toggle locking mechanism that covers the cannula shaft, where said toggle locking mechanism comprises of a hollow proximal cover segment and hollow distal cover segment linked through a central hinge;
  d) Wherein said proximal cover segment and distal cover segment are configured with vertical protruding locking faces above said central hinge;
  e) Wherein a proximal cover segment of said toggle locking mechanism is hingedly connected to said proximal hub by a proximal hinge and said distal cover segment of said toggle locking mechanism is hingedly connected to said distal end cap by a distal hinge;
  f) Wherein the proximal hinge, distal hinge and central hinge are arranged in the form of an inverted triangle formed by a line connecting said proximal and said distal hinges that lies parallel to the cannula shaft and said central hinge defining a vertex of the inverted triangle below said proximal and distal hinges.

The torsion spring is biased to maintain the toggle locking mechanism in a locked position. The torsion spring may be centered to and fitted on an inside of said centre hinge and comprises single or double coil loops on one or either side of the needle that allows the center hinge with coil loops to be lowered past said needle cannula shaft without interference by the cannula shaft.

The toggle locking mechanism may include a resilient wedge mechanism which is configured to be pressure activated to arrest said toggle locking mechanism in a temporary unlocked position to enable exposure of said cannula tip prior to the invasive procedure. The wedge mechanism may include a resilient wedge extension mounted on the distal cover segment or proximal cover segment, and the resilient wedge extension is located above the center hinge. The wedge may be configured to be clamped into a wedged-in position by spring force generated by the torsion spring, and the wedge is resiliently biased to dislocate from a wedged-in position when pressure applied by the torsion spring is reduced when said distal end cap pushes against a patient's skin.

The wedge may be integrated into a latch disk with single or multiple recess features on an inside face of the latch disk and a locking face on the wedge that allows it to wedge into/against a locking face on the proximal cover segment or distal cover segment when the wedge is pressure activated.

A further alternative description of the device and its operation is herein provided as follows. The segmented needle-protection cover may have at least five segments which are, in order from a point distal from the point on insertion of a needle:
  a) a hub element;
  b) a proximal first needle cannula cover segment;
  c) a central hinge;
  d) a distal second needle cannula cover segment; and
  e) a distal end cap.

The features of the present technology that may be further considered in this description may include facts wherein:
  1) This device is locked in rest/start position—all other devices is partly collapsed in rest
  2) The centre segment may be an element that is locked and that this locked central element is what separates the end cap from the hub and retains the end cap over and in a fixed position of protruding past the needle tip.
  3) The proximal and distal members aren't arms above the needle as in the other devices but bodies that completely covers the needle shaft (cannula.
  4) The way in which the members lock to form a rigid centre segment is a unique application of a (toggle locking mechanism) and is further described herein.
  5) The way in which the members can be manipulated to unlock to present the needle tip is preferably performed just prior to the injection
  6) A method and apparatus is provided for arresting (by wedging an element in-between the vertical locking faces) the device with the needle exposed.
  7) How the wedge escapes (when the tip touches the patents skin) is to free the lock to return to its home position upon release of the wedge.
  8) A second locking device manually activated to permanently lock the device to eliminate re-use.

Looking at a horizontal axis along which a needle would lie, passing through the needle cannula (a bore, not necessarily fully inclosing the needle, but nesting the needle in contact with an open groove in the a proximal first needle cannula cover segment and the distal second needle cannula cover segment, with the bottom of the needle length uncovered below the proximal first needle cannula cover segment and the distal second needle cannula cover segment) from the hub, past the proximal first needle cannula cover segment, the central hinge and the distal second needle cannula cover segment and into the distal end cap. The hub is in hinged connection to the proximal first needle cannula cover segment, and the distal second needle cannula cover segment is in hinged connection with the distal end cap. The elements operate with respect to rotation and alignment changes adjacent the hinges as follows, with the axis of the needle cannula being considered as approximately horizontal during a needle-safe alignment along the approximate horizontal alignment of a), b), d) and e):

1) When the proximal first needle cannula cover segment and the distal second needle cannula cover segment are in the safe, approximately horizontal alignment, the central hinge holds adjacent opposing faces of proximal first needle cannula cover segment and the distal second needle cannula cover segment in an abutting, locking (anti-rotational) position;

2) Rotation with respect to the hinge of the proximal first needle cannula cover segment (in a counter-clockwise movement with respect to the central hinge) and the distal second needle cannula cover segment (in a clockwise movement with respect to the central hinge) elevates tops of each of the opposing faces and elevates the central hinge and draws together the two most respectively distal faces or ends of the proximal first needle cannula cover segment and the distal second needle cannula cover segment, which are respectively adjacent the hub element and the distal end cap. This movement also shortens the distance between the distal end cap and the hub element, retracting the distal end cap towards the hub element.

3) Retraction of the distal end cap does not apply harmful sideways stress against any needle nesting in the needle cannula as rotation between both i) the proximal first needle cannula cover segment and hub and ii) the distal end cap and the distal second needle cannula cover segment causes both the proximal first needle cannula cover segment, the central hinge and the distal second needle cannula cover segment to elevate above the needle, removing the needle from the grooves in the proximal first needle cannula cover segment and the distal second needle cannula cover segment. This may momentarily expose the shaft of the needle, but not the pointed tip of the needle, except as the point of the needle extends beyond a distal end of the distal end cap as intended when the device is changed from the needle-safe position to the active needle insertion position.

4) During these movement, a rotating hinge between the hub element and the proximal first needle cannula cover segment, and a separate rotating hinge between the distal second needle cannula cover segment and the distal end cap are configured to keep the needle in the approximately horizontal position, with the portion of the needle cover cannula within the distal end cap remaining in the approximately horizontal alignment as the distal end cap retracts over the needle, exposing the needle tip during the conversion of the device to the active needle position. There is some modest stress placed on the needle from the rotation of respective elements, but essentially only at the hub element and the distal end cap. However, because little or no manual or finger (digit or digital) forces are directly applied to the end cap (where torsion stress would be most likely to deflect or stress the needle shaft), there is little significant deflecting stress applied to the needle shaft by the cover device when the needle is exposed to its active position during medical procedures, including insertion.

5) Downward force on the elevated central hinge (between the proximal first needle cannula cover segment and the distal second needle cannula cover segment lowers the central hinge, reverses all rotation of segments and extends the distal end cap over the needle tip, returning the device to its original needle safe position. The needle will again nest within the grooves in the proximal first needle cannula cover segment and the distal second needle cannula cover segment. The central hinge may or may not have a groove for nesting of the needle in the safe position. It is to be noted that the opposed adjacent faces of the proximal first needle cannula cover segment and the distal second needle cannula cover segment resist any deflection of the length of the device by downward pressure on the central hinge. This prevents any deflecting or bending stress being applied against the included needle during handling. In the following descriptions of the Figures, like numbers in different figures identify like elements.

Figures 1, 2, 3, 4, 5:
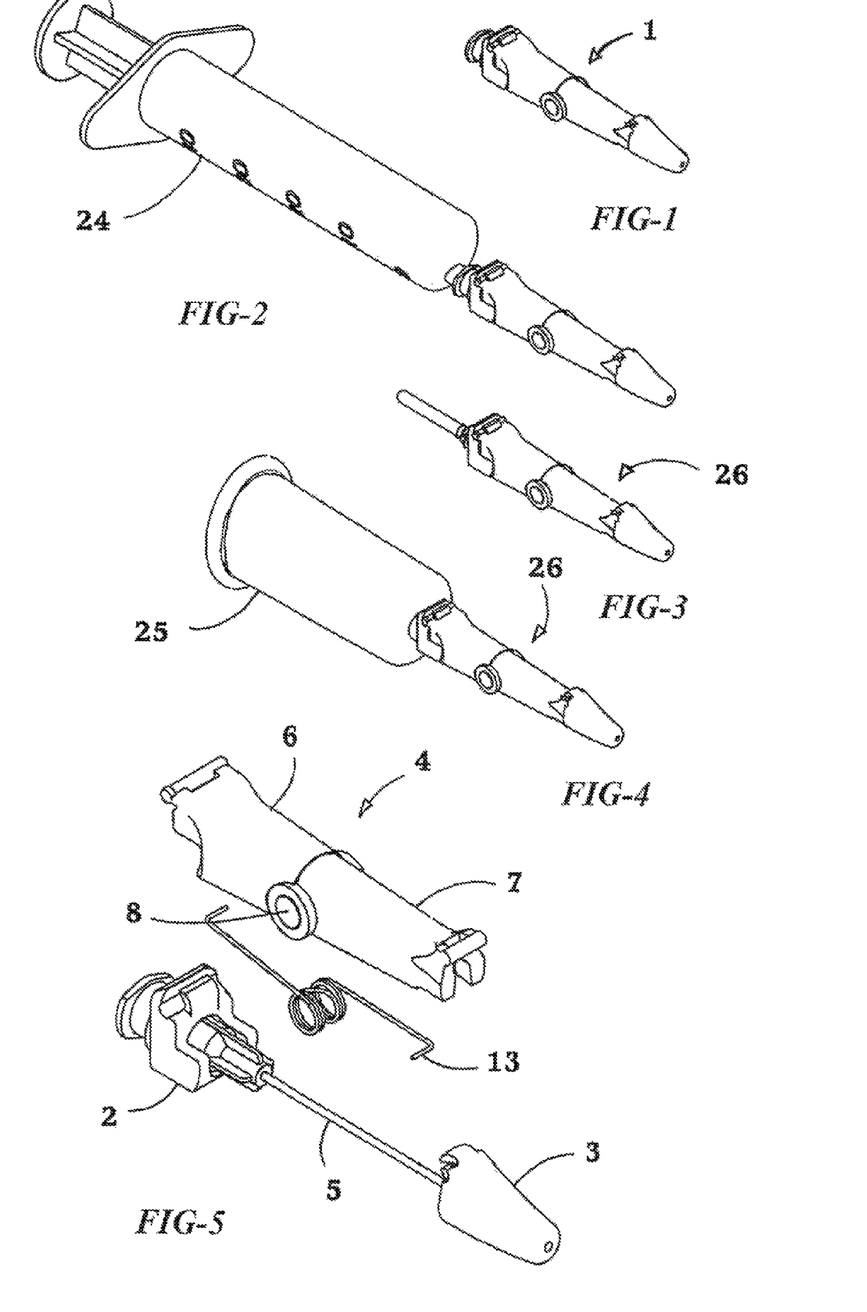
FIG. 1 is an isometric view of the device
FIG. 2 is an isometric view of the device mounted on a syringe
FIG. 3 is an isometric view of the device configured as a phlebotomy needle.
FIG. 4 is an isometric view of the phlebotomy configuration mounted on its holder
FIG. 5 is an exploded view of the device

FIG. 1 shows a perspective view of the Passive Safety Cover (1) in its locked and secured position.

FIG. 2 shows a perspective view of the Passive Safety Cover (1) attached to a syringe (24).

FIG. 3 shows a perspective view of an embodiment of the Passive Safety Device as a Phlebotomy Needle (26).

FIG. 4 shows a perspective view of the Phlebotomy embodiment (26) of FIG. 3 mounted to a tube holder (25).

FIG. 5 shows an isometric exploded view of the Passive Safety Cover. The Central toggle locking mechanism (4) consist of a hollow Proximal cover segment (6) linked to a hollow Distal cover segment (7) by means of a centrally mounted hinge (8). The unidirectional double torsion spring (13) urges the central toggle locking mechanism towards its locked, needle safe position. The Needle Hub (2) is hingedly connected to the proximal hinge of the central toggle locking mechanism (4). The distal end cap (3) slides over the needle cannula (5) and is also hingedly connected to the distal hinge of the centrally hinged segment.

Figure 6:
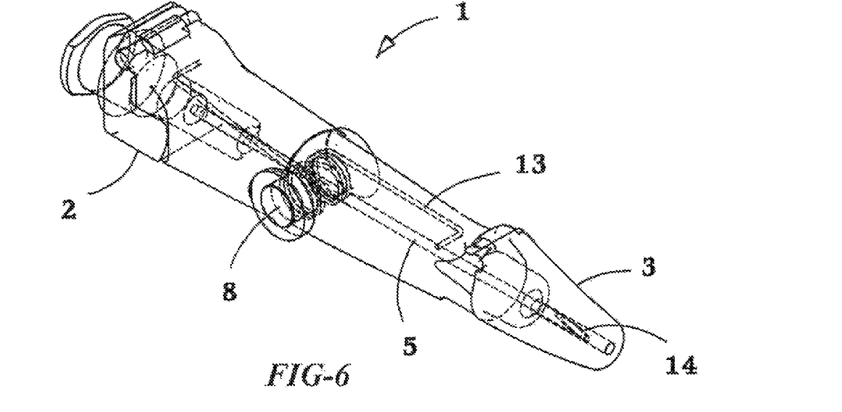
FIG. 6 is an isometric view with hidden detail

FIG. 6 is an isometric view of the device (1) in its locked, needle-safe position with the unidirectional double torsion spring (13) in place to maintain the central toggle locking mechanism in its extended and locked position where it separates the Hub (2) from the End Cap (3) which surrounds the Cannula shaft (5) and extends past the Cannula tip (14) within the distal end cap (3).

Figure 7:
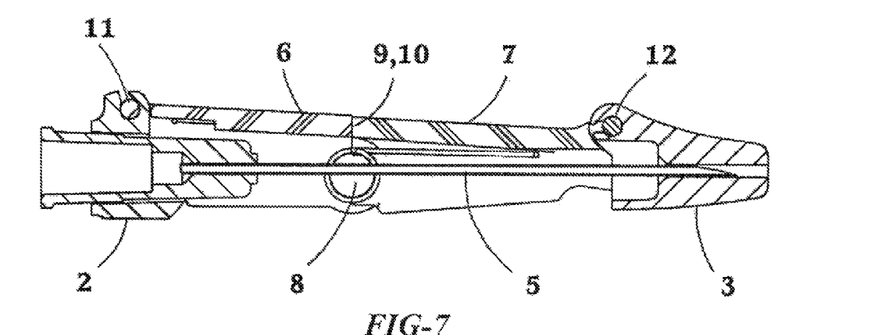
FIG. 7 is a sectioned view of the device

FIG. 7 is a sectioned view of the device (1) in its locked, needle safe position. The vertical locking faces, the opposed distal ends of the proximal cover segment and the opposed proximal end of the distal cover segment. The vertical locking faces (9, 10) are positioned above the central hinge (8) and is pushed against each other to retain the device in its locked position. The proximal hinge (11) connects the Hub (2) to the proximal cover segment (6) of the central toggle locking mechanism of which the Distal cover segment (7) connects to the End Cap (3) via the distal hinge (12). The relatively lower position of the central hinge (8) in relation to the needle cannula (5) is also shown.

Figure 8:
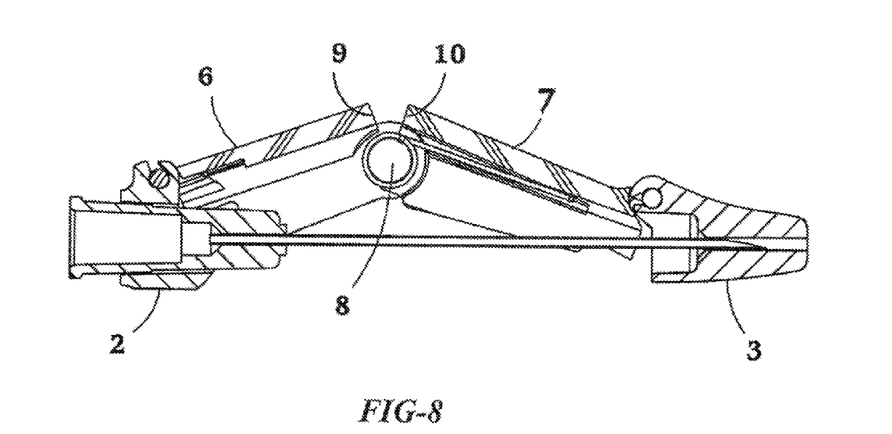
FIG. 8 is a sectioned view of the device with the central hinge of the toggle locking mechanism forced upwards to expose the locking faces.

FIG. 8 is a sectioned view of the device in a partly unlocked position. The central hinge (8) is advanced up to a position above the needle cannula (5 in FIG. 7) The vertical locking faces (9, 10) on the proximal and distal cover segments (6, 7) respectively are moving away from each other.

Figure 9:
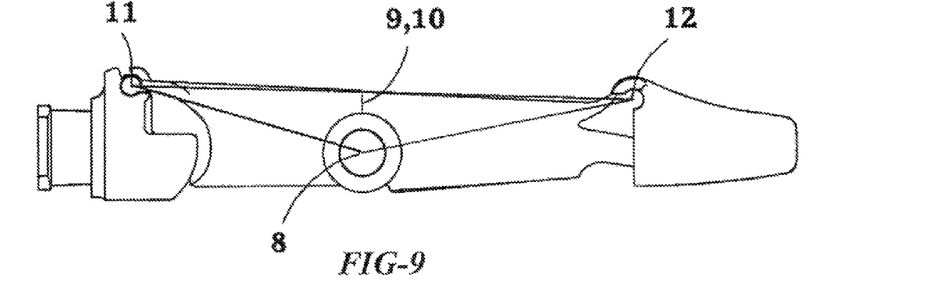
FIG. 9 is a side view of the device in its normal locked position with the central hinge below the proximal and distal hinges.

FIG. 9 is a side view of the device in its locked position. The proximal hinge (11) and distal hinge (12) are in line and generally above the height of the central hinge (8) with the vertical locking faces (9, 10) pushed against one another. The hinges (11 and 12) may be living hinges or pins passing through securing holes in the structural elements.

Figure 10:
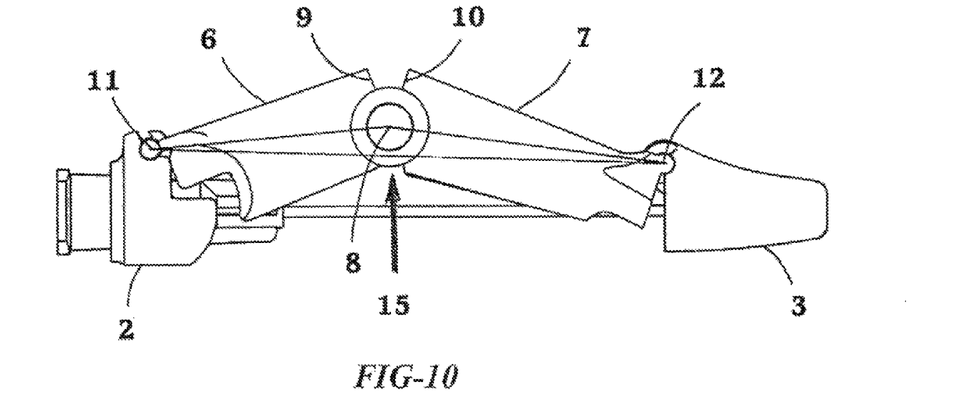
FIG. 10 is a side view of the device with the central hinge forced up to a position higher than the proximal and distal hinges.

FIG. 10 is a side view of the device with a digital (fingered) upwards force (15) applied to pull or push the central hinge (8) to a position above the cannula (5 in FIG. 6), proximal hinge (11) and distal hinge (12). The proximal cover segment's (6) vertical locking face (9) is parting from the vertical locking face (10) of the distal cover segment (7) as the centrally hinged section unlocks and elevates.

Figure 11:
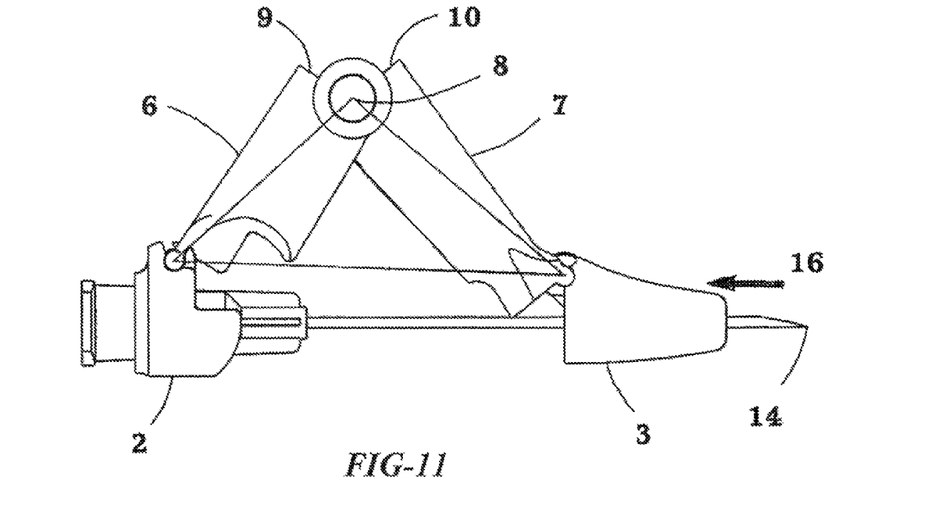
FIG. 11 is a side view of the device in its temporary unlocked position which shows a digital force being applied to the distal end to expose the needle tip.

FIG. 11 is a side view of the device in its unlocked position where a digital (fingered) axial force (16) causes the toggle locking mechanism to collapse towards the hub (2) or the end cap (3) to retract, thereby exposing the cannula tip (14)

Figure 12:
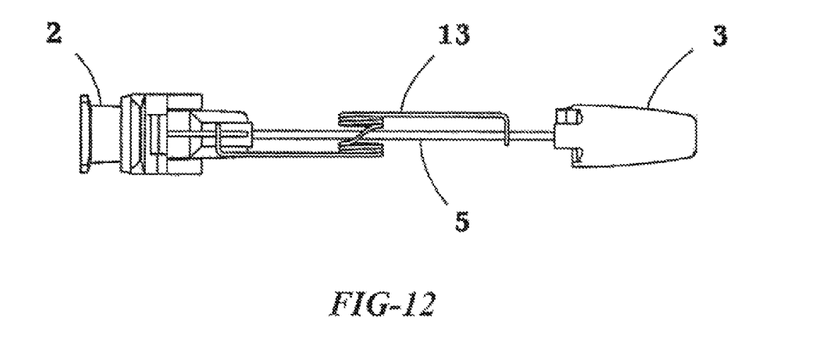
FIG. 12 is a top view with the toggle locking mechanism removed, showing the position of the unidirectional double torsion spring with its coil loops on either side of the needle cannula.

FIG. 12 is an open top view of the device with the toggle central locking mechanism removed to show the position of the unidirectional double torsion spring (13) with its with its coil loops on either side of the needle cannula (5).

Figure 13:
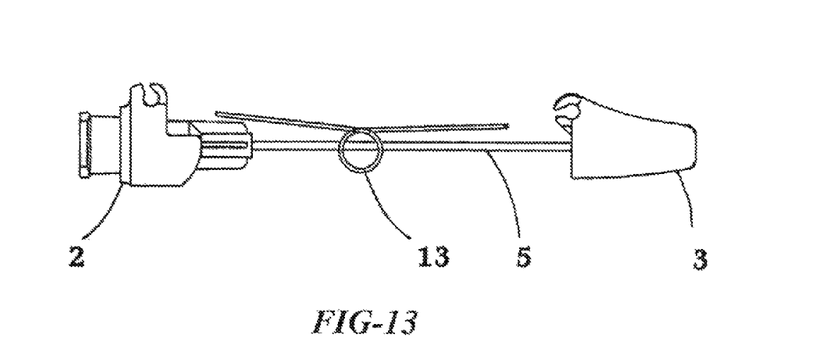
FIG. 13 is a side view showing the spring coils over the cannula center.

FIG. 13 is a side view of the device with the toggle locking mechanism removed to show the position of the unidirectional double torsion spring (13) in relation to the needle cannula (5).

Figure 14:
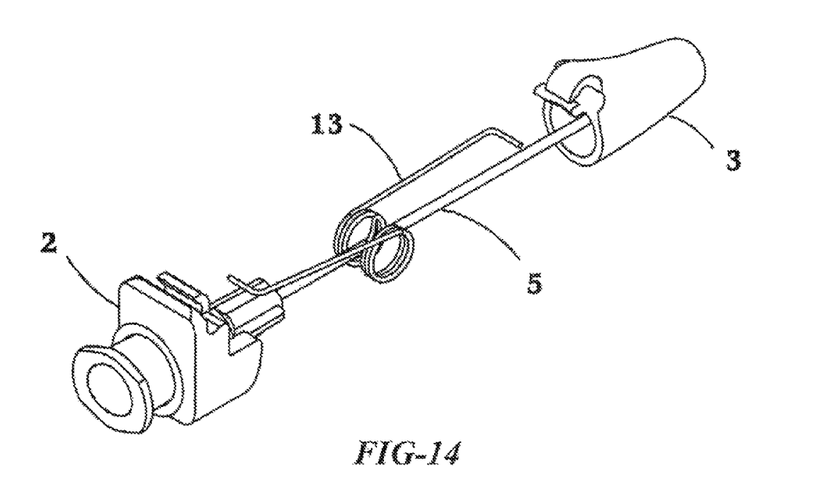
FIG. 14 is an isometric view of the spring position relative to the needle canulla.

FIG. 14 is an isometric view of the device with the central toggle locking mechanism removed to show the position of the unidirectional double torsion spring (13) between the Hub (2) and distal End Cap (3) and over the needle cannula (5).

Figures 15, 16:
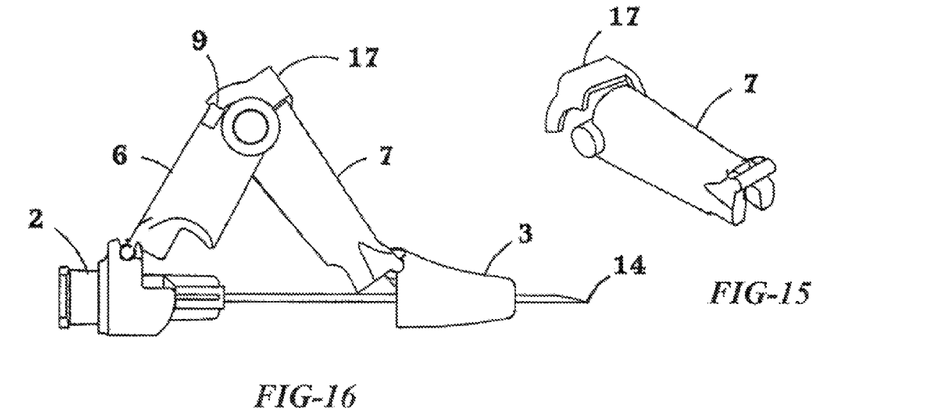
FIG. 15 is an isometric view of the distal cover segment with the resiliently biased or spring loaded wedge extension.
FIG. 16 is a side view of the device in its temporary unlocked position with the resiliently biased wedge pushed up against the locking face of the distal cover segment.

FIG. 15 shows an angular configuration of the distal cover segment (7) of the toggle locking mechanism with a resilient wedge extension (17).

FIG. 16 shows a side view of the device in an unlocked and arrested needle (14) delivery position. The resilient wedge extension (17) is engaged and wedges against the vertical locking face (9) of the proximal cover segment (6) of the central toggle locking mechanism. In this position, the end cap (3) has moved towards the hub (2) thereby exposing the needle tip (14).

Figure 17:
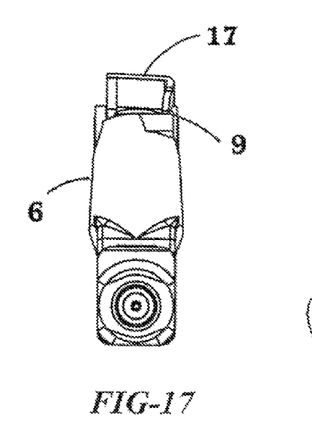
FIG. 17 is a rear view of the device in its temporary unlocked position with the resiliently biased wedge pushed up against the locking face

FIG. 17 is a rear view of the device in the unlocked and arrested delivery position. The resilient wedge extension (17) is shown under tension after being forced in position by an external digital force and pushing up against the vertical locking face (9) of the proximal cover segment (6), exposing the needle tip.

Figure 18:
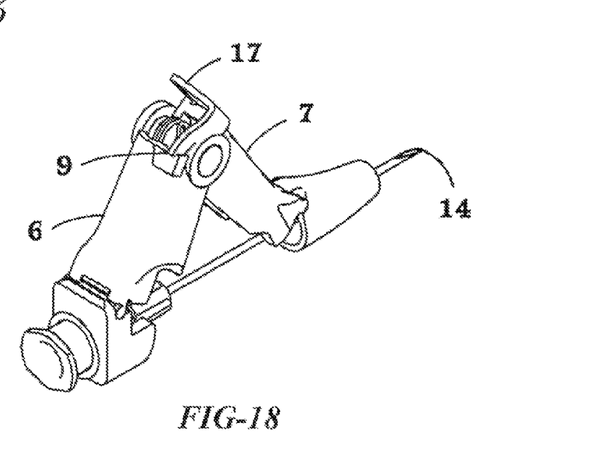
FIG. 18 is an isometric view of the device in its temporary unlocked position with the resiliently biased wedge pushed up against the locking face

FIG. 18 is an isometric view again showing the device in its unlocked and arrested delivery position. The unidirectional double torsion spring (not shown, but see 13 in FIGS. 13 and 14) force urges the central toggle locking mechanism to extend, thus clamping and retaining the resilient wedge extension (17) in this position.

Figure 19:
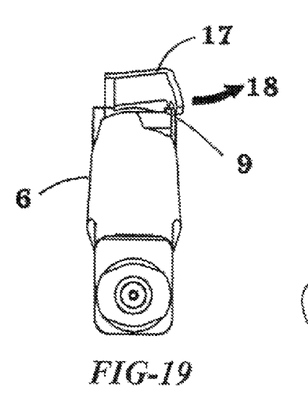
FIG. 19 is a rear view of the device shown with the resiliently biased wedge dislocated by a digital force applied to the distal end cap.

FIG. 19 is a rear view of the device with the resiliently biased wedge escaping (18) at the introduction of the external digital force (16).

Figure 20:
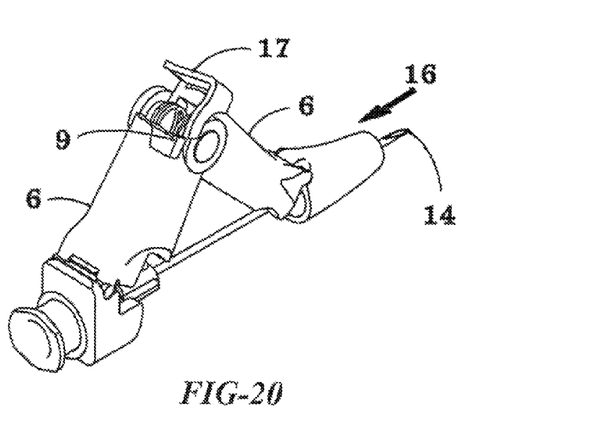
FIG. 20 is an isometric view of the device shown with the resiliently biased wedge dislocated by a digital force applied to the distal end cap.

FIG. 20 is an isometric view of the device and shows a digital, axial force (16) being exerted onto the end cap (3) in FIG. 16). This would take place as the patient's skin pushes onto the end cap (3). This action relieves the pressure between the vertical locking face (9) and resiliently biased wedge (17) and causes the resiliently biased wedge (17) to move as its tension is released.

Figure 21:
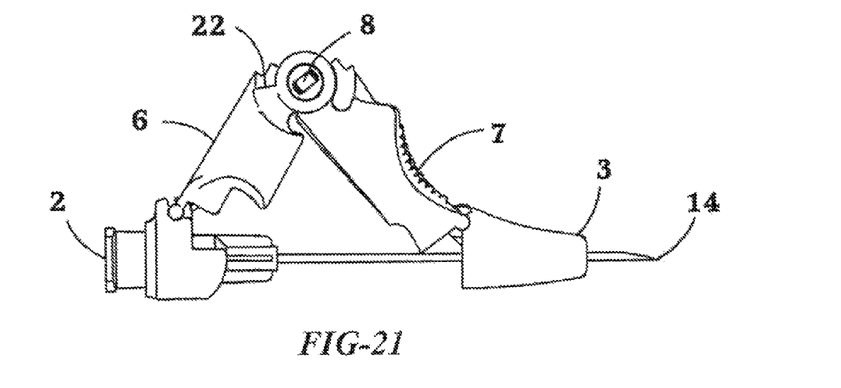
FIG. 21 is a side view of the device with the latch disk hidden to show the exposed locking faces.

FIG. 21 is an embodiment of this device in its arrested delivery position where the wedge is integrated into a latch disk (not shown) and the locking face is extended (22) to the side of the proximal cover segment (6). The latch disk is hidden for clarity.

Figure 22:
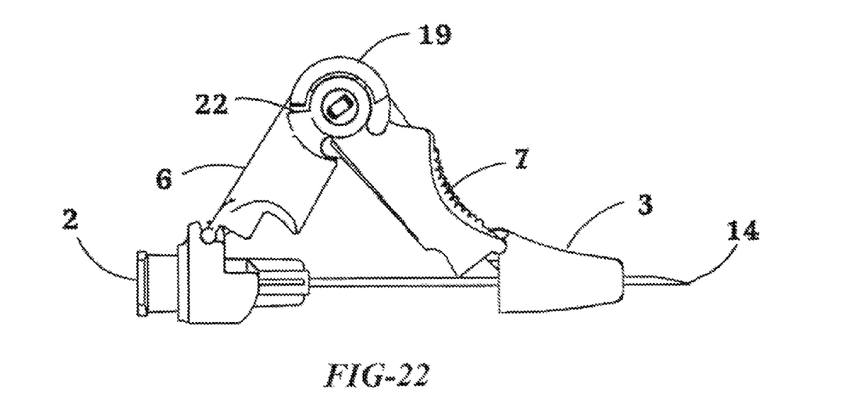
FIG. 22 is a side view of the device with a section through the latch disk cover exposing the wedge in its arrested position.

FIG. 22 is a side view of the device in its arrested position with the resiliently biased latch disk (19) wedged up against the extended locking face (22) on the proximal cover segment (6).

Figure 23:
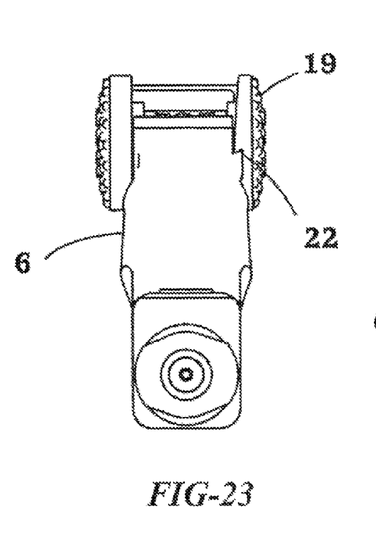
FIG. 23 is a rear view of the device showing the latch disk in its arrested position.

FIG. 23 is a rear view of the device in its arrested position again showing the resiliently biased latch disk (19) wedged up against the extended locking face (22) on the proximal cover segment (6).

Figure 24:
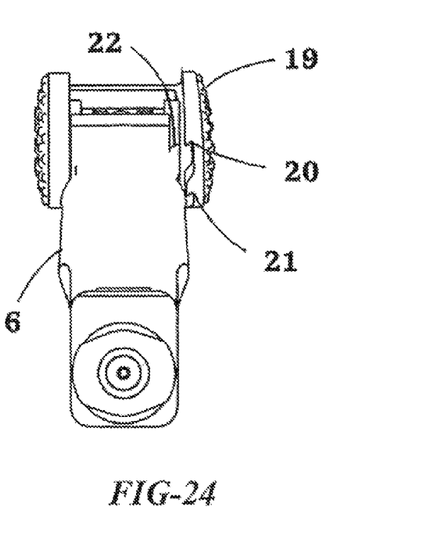
FIG. 24 is a rear view of the device showing the latch disk dislocated by a digital force applied to the distal end cap.

FIG. 24 is a rear view of the device with the resiliently biased latch disk (19) in its escaped position after the introduction of an external digital force.

Figures 25, 26, 27, 28, 29:
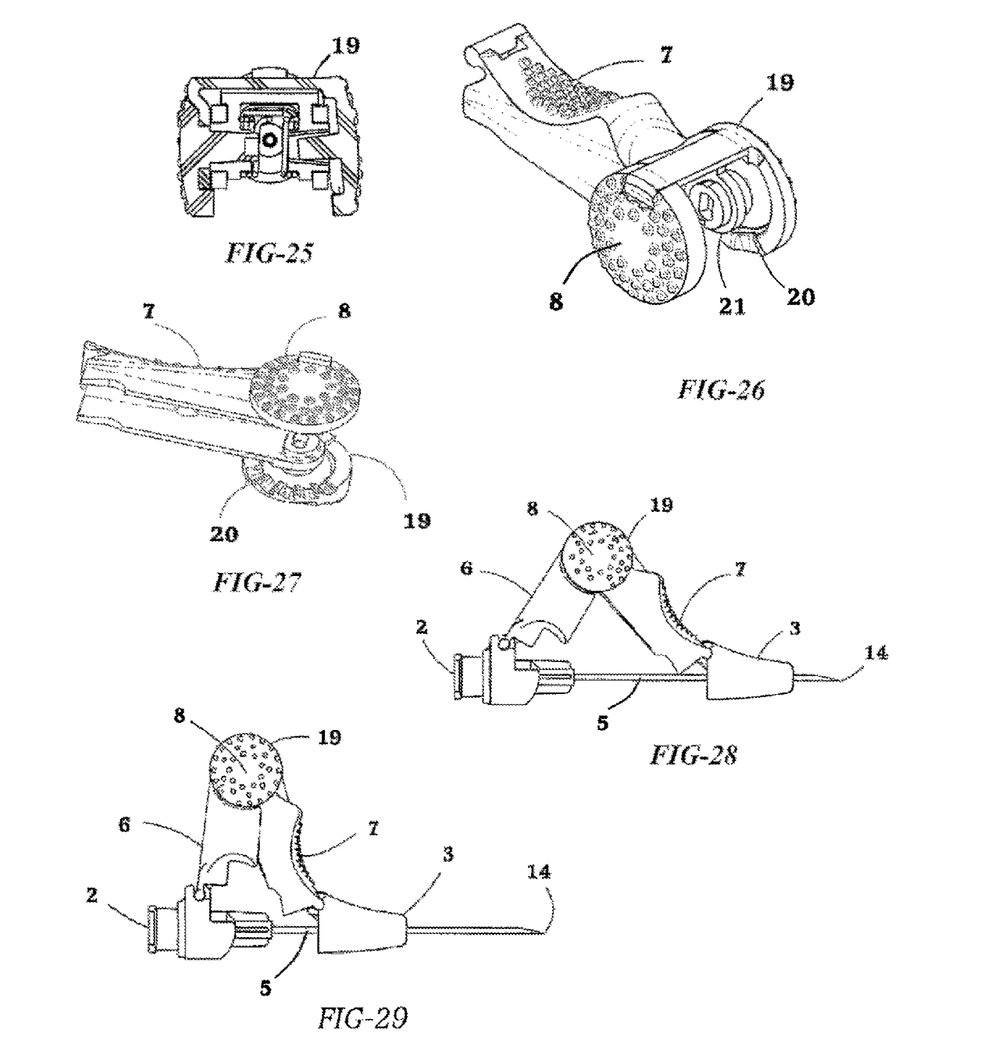
FIG. 25 is a sectioned view through the centre hinge showing the latch disk in its dislocated position.
FIG. 26 is an isometric view of the distal cover segment with the latch disk secured in place by the retention disk.
FIG. 27 is an isometric view showing the latch disk with multiple recess features.
FIG. 28 is a side view of the device in its first temporally recessed and arrested position exposing the tip of the needle canulla.
FIG. 29 is a side view of the device in its second temporally recessed and arrested position exposing a longer portion of the needle canulla.

FIG. 25 is a cross sectioned view of the resiliently biased latch disk (19) in its escaped position.

FIG. 26 is an isometric view of the distal cover segment (7) with the resiliently biased Latch disk (19) mounted on it. The latch disk (19) has multiple recess features (20, 21) on its inside face that allows it to wedge into/against the proximal cover segment's said locking face extension when digitally activated. The multiple features add convenience for the user to selectively choose how far they need the needle (not shown) to extend past said distal end cap (not shown).

FIG. 27 is an isometric view showing the distal cover segment (7), the central hinge (8) and the latch disk (19) with multiple recess features (20).

FIG. 28 is a side view of the arrested device at its first recessed feature (20 in FIG. 16) thereby exposing a small portion of the needle cannula (5 in earlier Figures).

FIG. 29 is a side view of the arrested device at its second recessed feature (21 in FIG. 16) thereby exposing a longer section of the needle tip (14) out of the end cap (3) from the cannula (5 in earlier Figures).

Figure 30:
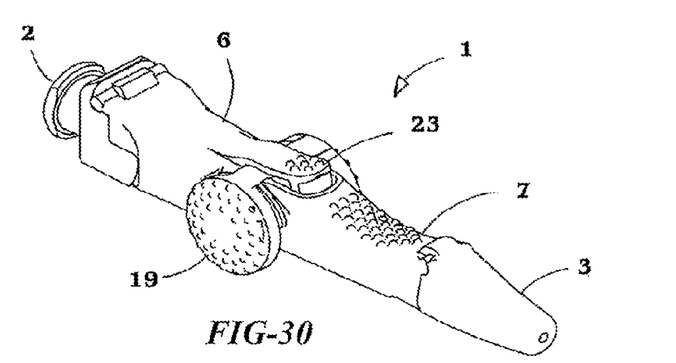
FIG. 30 is an isometric view of the device with the double lock clip in its inactivated state.

FIG. 30 is an isometric view of an embodiment of the device in its locked position with an additional second locking feature (23) which is integrated into the proximal cover segment (6). This lock is applied to permanently lock the device after the invasive procedure to eliminate re-use of the device. The needle tip (14) is completely extended past the end cap (3).

Figure 31:
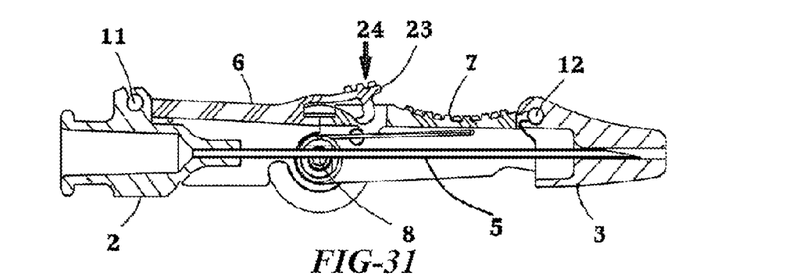
FIG. 31 is a sectioned side view of the device with the double lock clip in its inactivated state.

FIG. 31 is a sectioned side view of the device showing the direction of an external digital force (24) to permanently lock it against re-use.

Figure 32:
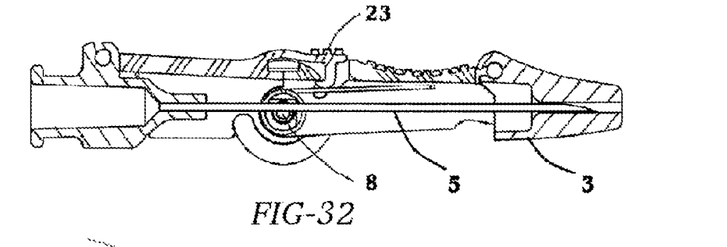
FIG. 32 is a sectioned side view of the device with the double lock clip in its activated state.

FIG. 32 is a sectioned side view of the device showing the second lock (23) applied thus permanently locking the proximal cover segment (6) onto the distal cover segment (7) as shown in FIG. 30.

Figure 33:
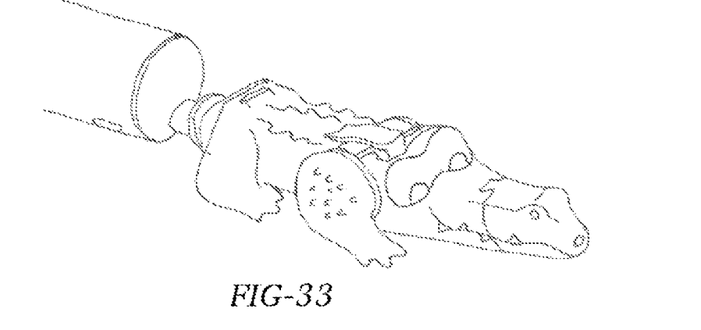
FIG. 33 shows a perspective view of a device according to the present invention having a design feature for use with children, in this case the image of an alligator moulded into the front of the device.

FIG. 33 shows a perspective view of a device according to the present invention having a design feature for use with children, in this case the image of an alligator moulded into the front of the device.

The above descriptions enable practice of the generic scope of the claims. It is to be noted that specific shapes, materials and relative dimensions in the disclosure may be altered to implement the device in varying medical fields without altering the underlying nature and performance of the invention.

What is claimed is:

1. A segmented safety cover comprising: a) a proximal segment combined with a needle hub; b) a needle cannula that extends from the proximal needle hub to a distal sharpened end; c) a distal end cap with a hollow bore through which the needle cannula passes; d) a centrally mounted toggle locking mechanism, separating the proximal needle hub from the distal end cap, hingedly connected to both and maintaining the segmented safety cover in a position where it completely covers a needle tip; e) wherein the toggle locking mechanism is resistively bias-assisted and comprises a proximal cover segment and a distal cover segment which overlay the needle cannula and is linked together through a central hinge; f) said proximal cover segment and said distal cover segment of said toggle locking mechanism being configured with abutting faces that contact each other above said central hinge when the segmented safety cover is in a safety mode; g) wherein the proximal cover segment is connected to the hub via a proximal hinge and the distal cover segment is connected to the end cap via a distal hinge; and h) wherein the proximal hinge, abutting faces and distal hinge are in line and the central hinge is below the abutting faces in the safe mode so that a force exerted on the distal end cap is translated onto the abutting faces above the central hinge thereby maintaining the device in its locked state, without exposing a needle out of the needle cannula in the distal end cap from within the needle cannula; wherein the torsion spring comprises a double coil spring, wherein a first one coil of the double coil spring is on a first side of the needle cannula and a second one coil of the double coil spring is on a second and opposite side of the needle cannula with respect to the first coil that allows the center hinge to be lowered past said needle cannula without interference by the needle cannula.

2. The segmented safety cover of claim 1 wherein the proximal hinge, distal hinge and central hinge are configured to form a triangular configuration when the segmented safety cover is in a delivery mode for the needle within the needle cannula, and the distal cover segment and the distal end cap are configured to slide with respect to the needle within the hollow bore.

3. The segmented safety cap of claim 2 wherein upon forming the triangular configuration, the distal end cap is configured to retract over the needle and towards the needle hub, and relative to the distal cover, appears to rotate away from the distal cover segment and expose the injection end of the needle.

4. The segmented safety cover of claim 2 wherein in the safety mode, the distal cover segment and proximal cover segment are in a locked mode, resisting movement of the distal cover segment and the proximal cover segment by the torsion spring.

5. The segmented safety cover of claim 4 wherein two manually operated pressure plates that overlap sides of the distal cover segment and the proximal cover segment are configured to unlock the locked mode when pressure is applied to the two pressure plates.

6. The segmented safety cover of claim 5 where said pressure plates are resiliently biased to dislocate from the unlocked mode to return to a locked ready mode when triggered by said distal end cap when it pushes against a patient's skin during the injection procedure, wherein said dislocated pressure plates release the segmented safety cover to return to its original locked mode as the needle is withdrawn from the patient.

7. The segmented safety cover of claim 5 wherein a second locking mechanism configured to establish the locked mode extends across a top of the abutting faces of the distal cover segment and the proximal cover segment.

8. The segmented safety cover of claim 6 wherein the second locking mechanism comprises a clip on the proximal cover segment that snaps into a receiving opening on the distal cover segment.

9. The segmented safety cover of claim 6 wherein the second locking mechanism comprises a clip on the distal segment that snaps into a receiving opening on the proximal segment.

10. The segmented safety cover of claim 1 wherein the double coil spring comprises a first extension of the double coil spring extending approximately parallel to the distal segment in the safety mode, and a second extension of the double coil spring extending approximately parallel to the proximal segment in the safety mode.

11. The segmented safety cover of claim 2 wherein the double coil spring comprises a first extension of the double coil spring extending approximately parallel to the distal segment in the safety mode, and a second extension of the double coil spring extending approximately parallel to the proximal segment in the safety mode.

12. The segmented safety cover of claim 1 wherein the needle is present within the cover, and the segmented safety cover is configured so that the pointed injection end of the needle is completely covered by the distal end cap when the torsion spring is secured in the safety mode, and the pointed injection end of the needle is exposed out of the distal end cap when the safety mode is removed and compressive force applied by the torsion spring retracts the distal end cap by rotation of both the proximal cover segment and the distal cover segment about the central hinge.

13. The segmented safety cap of claim 1 where said safety cover is configured having a design feature for use with children, with the image of an animal or other object moulded in front of the device to act as a paediatric distracting feature.

14. A method for enabling injection of fluids using the segmented safety cover with a needle present within the cover of claim 2 comprising applying force to both the proximal cover segment and the distal cover segment from the torsion spring to elevate the central hinge and retract the distal end cap to slide the cannula within the distal end cap over the needle to expose the needle; wherein the proximal hinge, distal hinge and central hinge are arranged in the form of an inverted triangle formed by a line connecting said proximal and said distal hinges that lies parallel to the cannula shaft and said central hinge defining a vertex of the inverted triangle below said proximal and distal hinges, and an exposure position for a needle within the cannula is created only when the central hinge is elevated above the a line connecting said proximal and said distal hinges from the position of the central hinge as the vertex of the inverted triangle.

15. A segmented safety cover comprising:
a) a proximal segment fixed with a needle hub, said proximal segment also being integrated with a syringe body or a blood collecting needle; b) a distal end cap with a hollow bore that covers a cannula shaft through which a needle may pass; c) a rigidly interlocked, torsion spring assisted centrally hinged toggle locking mechanism that covers the cannula shaft, where said center segment comprises a hollow proximal cover segment and distal hollow cover segment linked through a central hinge; d) wherein said proximal cover segment and distal cover segment are configured with vertical protruding abutting locking faces above said central hinge; e) wherein a proximal cover segment of said central toggle locking mechanism is hingedly connected to said proximal segment by a proximal hinge and said distal cover segment of said central toggle locking mechanism is hingedly connected to said distal end cap by a distal hinge; f) wherein the proximal hinge, distal hinge and central hinge are arranged in the form of an inverted triangle formed by a line connecting said proximal and said distal hinges that lies parallel to the cannula shaft and said central hinge defining a vertex of the inverted triangle below said proximal and distal hinges; and g) wherein an exposure position for a needle from within the cannula shaft is created only when the central hinge is elevated above the line connecting said proximal and said distal hinges from the position of the central hinge as the vertex of the inverted triangle; wherein the torsion spring comprises a double coil spring, wherein a first one coil of the double coil spring is on a first side of the cannula shaft and a second one coil of the double coil spring is on a second and opposite side of the cannula shaft with respect to the first coil that allows the center hinge to be lowered past said cannula shaft without interference by the cannula shaft.

16. The segmented safety cover of claim 15 wherein said torsion spring is biased to maintain the central toggle locking mechanism in a locked position.

17. The segmented safety cover of claim 15 where said torsion spring is centered to and fitted on an inside of said center hinge.

18. The segmented safety cover according to claim 15 wherein said central toggle locking mechanism includes a resiliently biased wedge mechanism which is configured to be pressure activated to arrest said toggle locking mechanism in a temporary unlocked position to enable exposure of said cannula tip prior to the invasive procedure.

19. The segmented safety cover according to claim 18 wherein said wedge mechanism comprises a resiliently biased wedge extension mounted on the distal cover segment or proximal cover segment, and the spring-locked wedge is located above the center hinge.

20. The segmented safety cap of claim 19 wherein said wedge is configured to be clamped into a wedged-in position by spring force generated by the torsion spring.

21. The segmented safety cap of claim 19 where the wedge is configured to be resiliently biased to dislocate from a wedged-in position when pressure applied by the torsion spring is reduced when said distal end cap pushes against a patient's skin.

22. The segmented safety cap of claim 18 wherein said resiliently biased wedge is integrated into a latch disk with single or multiple recess features on an inside face of the latch disk and a locking face on the wedge that allows it to wedge into/ against a locking face on the proximal cover segment or distal cover segment when the wedge is pressure activated.

\* \* \* \* \*